United States Patent
Song et al.

(10) Patent No.: US 11,278,464 B2
(45) Date of Patent: Mar. 22, 2022

(54) EXOSKELETON FINGER REHABILITATION TRAINING APPARATUS

(71) Applicant: SOUTHEAST UNIVERSITY, Nanjing (CN)

(72) Inventors: Aiguo Song, Nanjing (CN); Jianwei Lai, Nanjing (CN); Huijun Li, Nanjing (CN); Jianqing Li, Nanjing (CN); Baoguo Xu, Nanjing (CN); Hong Zeng, Nanjing (CN); Jun Zhang, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 0 days.

(21) Appl. No.: 17/416,468

(22) PCT Filed: Mar. 21, 2019

(86) PCT No.: PCT/CN2019/079093
§ 371 (c)(1),
(2) Date: Jun. 19, 2021

(87) PCT Pub. No.: WO2020/124837
PCT Pub. Date: Jun. 25, 2020

(65) Prior Publication Data
US 2022/0040028 A1    Feb. 10, 2022

(30) Foreign Application Priority Data
Dec. 20, 2018  (CN) .......................... 201811561691.7

(51) Int. Cl.
*A61H 1/02*    (2006.01)
*G16H 20/30*   (2018.01)

(52) U.S. Cl.
CPC .......... *A61H 1/0288* (2013.01); *G16H 20/30* (2018.01); *A61H 2201/1215* (2013.01);
(Continued)

(58) Field of Classification Search
CPC ...... A61H 1/02; A61H 1/0285; A61H 1/0288; A61H 2201/165; A61H 2205/065; A61H 2205/067; B25J 9/0006; B25J 13/02
See application file for complete search history.

(56) References Cited

U.S. PATENT DOCUMENTS 3,756,222 A * 9/1973 Ketchum ............. A61H 1/0288
                                          601/40
5,697,892 A * 12/1997 Torgerson ............ A61H 1/0288
                                          601/40
(Continued)

FOREIGN PATENT DOCUMENTS

CN    203724417 U   7/2014
CN    107184370 A   9/2017
(Continued)

*Primary Examiner* — Justine R Yu
*Assistant Examiner* — Christopher E Miller
(74) *Attorney, Agent, or Firm* — Bayramoglu Law Offices LLC

(57) ABSTRACT

An exoskeleton finger rehabilitation training apparatus includes a housing. A first motor and a second motor are disposed inside the housing. A direction of an output shaft of the first motor is opposite to a direction of an output shaft of the second motor. The output shaft of the first motor is provided with a first motor gear. A right side of the first motor gear is engaged with a first transmission gear. An edge of the first transmission gear is sequentially connected to an index finger sleeve and a middle finger sleeve that are axially arranged. The output shaft of the second motor is provided with a second motor gear. A right side of the second motor gear is engaged with a second transmission gear. An edge of the second transmission gear is sequentially connected to a pinky sleeve and a ring finger sleeve that are axially arranged.

11 Claims, 3 Drawing Sheets

(52) U.S. Cl.
CPC .......... *A61H 2201/149* (2013.01); *A61H 2201/1638* (2013.01); *A61H 2201/1676* (2013.01); *A61H 2201/5007* (2013.01); *A61H 2201/5069* (2013.01); *A61H 2201/5071* (2013.01)

(56) References Cited

U.S. PATENT DOCUMENTS

| | | | |
|---|---|---|---|
| 10,449,677 B1* | 10/2019 | Al Najjar | B25J 15/0009 |
| 2012/0059291 A1* | 3/2012 | Nguyen | A61H 1/0288 |
| | | | 601/40 |
| 2014/0277582 A1* | 9/2014 | Leuthardt | A61F 2/54 |
| | | | 623/25 |
| 2015/0112451 A1* | 4/2015 | Dechev | A61F 2/54 |
| | | | 623/63 |
| 2017/0042704 A1* | 2/2017 | Ryu | A61H 1/0288 |
| 2019/0029909 A1* | 1/2019 | Perry | A61H 1/0288 |
| 2019/0336382 A1* | 11/2019 | Lan | A61H 1/0266 |
| 2021/0401657 A1* | 12/2021 | Song | A61H 1/0288 |

FOREIGN PATENT DOCUMENTS

| | | |
|---|---|---|
| CN | 107233188 A | 10/2017 |
| CN | 108814895 A | 11/2018 |
| KR | 20170086238 A | 7/2017 |
| KR | 20170106039 A | 9/2017 |
| WO | 2015144705 A1 | 10/2015 |
| WO | 2017072463 A1 | 5/2017 |

\* cited by examiner

EXOSKELETON FINGER REHABILITATION TRAINING APPARATUS

CROSS REFERENCE TO THE RELATED APPLICATIONS

This application is the national stage entry of International Application No. PCT/CN2019/079093, filed on Mar. 21, 2019, which is based upon and claims priority to Chinese Patent Application No. 201811561691.7 filed on Dec. 20, 2018, the entire contents of which are incorporated herein by reference.

TECHNICAL FIELD

The present invention relates to the field of medical rehabilitation devices, and specifically, to an exoskeleton finger rehabilitation training apparatus.

BACKGROUND

A cerebral stroke is a type of disease that causes pathological changes in the cerebral artery and the venous system due to various reasons. As an important organ of human beings, hands are an indispensable part of life and work. For hand paralysis caused by the cerebral stroke, relevant research shows that normal functions can be restored after rehabilitation training.

Existing hand rehabilitation treatment is mainly physical training treatment performed by professional doctors. Such treatment methods have three disadvantages:

1. A treatment effect depends on experience of doctors, and different doctors have different treatment effects.
2. Different doctors have different treatment effects, and only a very small number of people can get professional treatment.
3. A treatment environment is restricted, and a treatment time is very limited.

SUMMARY

To resolve the foregoing problems, the present invention provides an exoskeleton finger rehabilitation training apparatus, which assists a stroke patient in rehabilitation training of finger extension and clenching, and is safe and reliable to use.

Technical solutions: The present invention provides an exoskeleton finger rehabilitation training apparatus. The apparatus includes a housing and a first motor and a second motor that are disposed inside the housing, a direction of an output shaft of the first motor being opposite to a direction of an output shaft of the second motor.

The output shaft of the first motor is provided with a first motor gear, a right side of the first motor gear is engaged with a first transmission gear, and an edge of the first transmission gear is sequentially connected to an index finger sleeve and a middle finger sleeve that are axially arranged. The output shaft of the second motor is provided with a second motor gear, a right side of the second motor gear is engaged with a second transmission gear, and an edge of the second transmission gear is sequentially connected to a pinky sleeve and a ring finger sleeve that are axially arranged.

An outer wall of the housing is fixed to a first support arm configured to mount a rotary shaft of the first transmission gear and a second support arm configured to mount a rotary shaft of the second transmission gear.

The support base is further provided with a thumb sleeve, and relative positions of the thumb sleeve, the index finger sleeve, the middle finger sleeve, the ring finger sleeve, and the pinky sleeve conform to an arrangement of human fingers.

Further, the first motor and the second motor are sequentially arranged side by side from left to right, the first transmission gear is an arc-shaped external gear, and the second transmission gear is an arc-shaped internal gear.

Further, the first transmission gear is connected to the rotary shaft of the first transmission gear by using a first radius-connecting rod, and the second transmission gear is connected to the rotary shaft of the second transmission gear by using a second radius-connecting rod.

Further, the first radius-connecting rod and the index finger sleeve are separately located at two arc ends of the first transmission gear, and the second radius-connecting rod and the pinky sleeve are separately located at two arc ends of the second transmission gear.

Further, the housing is provided with a first passage through which the first transmission gear passes and a second passage through which the second transmission gear passes.

Further, the first transmission gear is provided with a first rotation limiting protrusion between a first passage and the index finger sleeve, and the second transmission gear is provided with a second rotation limiting protrusion between a second passage and the pinky sleeve.

Further, the exoskeleton finger rehabilitation training apparatus further includes a control system. The control system includes: a single-chip microcomputer, an encoder configured to measure a rotating speed of the first motor and a rotating speed of the second motor, a first angle sensor fixed to the first support arm and sleeved on the rotary shaft of the first transmission gear, a second angle sensor fixed to the second support arm and sleeved on the rotary shaft of the second transmission gear, and five pressure sensors respectively disposed inside the thumb sleeve, the index finger sleeve, the middle finger sleeve, the ring finger sleeve, and the pinky sleeve. The encoder, the first angle sensor, the second angle sensor, and the pressure sensors each transmit a measurement signal to the single-chip microcomputer, and the single-chip microcomputer outputs, to the first motor and the second motor, control signals used to control the rotating speeds of the motors.

Further, a model of the single-chip microcomputer is STM32F103, and a model of the first angle sensor and the second angle sensor is SV01A103AEA01R00.

Beneficial effects: The present invention is suitable for helping a patient with hand hemiplegia caused by a cerebral stroke perform active and passive rehabilitation training, and has the following advantages:

a. The exoskeleton finger rehabilitation training apparatus includes the index finger sleeve and the middle finger sleeve that are controlled by using the first transmission gear, and the ring finger sleeve and the pinky sleeve that are controlled by using the second transmission gear. The apparatus can effectively fit movement trajectories of the fingers, assist a stroke patient to extend and clench the fingers, and put small pressure on the fingers of the patient. The apparatus is light and does not cause secondary injury.

b. Force outputs are precisely controlled by the pressure sensors, and extreme rotation positions of the finger sleeves are precisely controlled by the angle sensors. Therefore, the apparatus is more stable, safe, and reliable.

In the figures: 1—housing, 2—first motor, 3—second motor, 4—first motor gear, 5—first transmission gear, 6—index finger sleeve, 7—middle finger sleeve, 8—second motor gear, 9—second transmission gear, 10—pinky sleeve, 11—ring finger sleeve, 12—first support arm, 13—second support arm, 14—thumb sleeve, 15—first radius-connecting rod, 16—second radius-connecting rod, 17—first angle sensor, 18—second angle sensor, 19—pressure sensor.

DETAILED DESCRIPTION OF THE EMBODIMENTS

Figure 1:
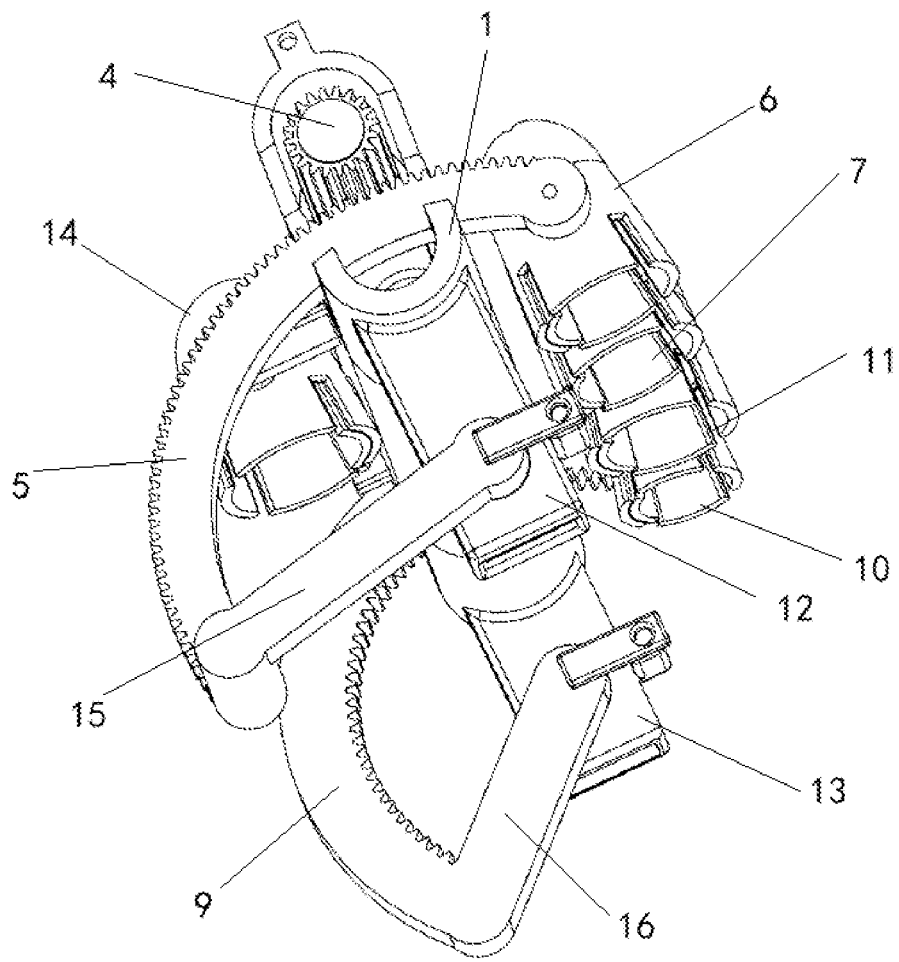
FIG. 1 is a schematic diagram of a three-dimensional structure of the present invention.
Figure 2:
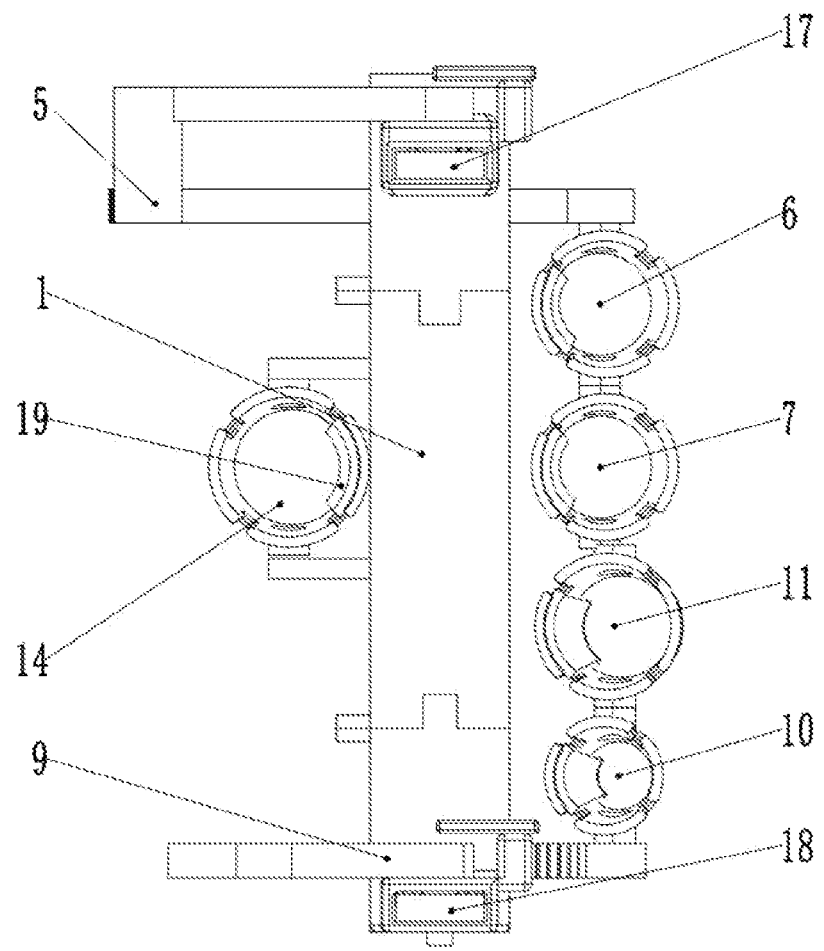
FIG. 2 is a front view of the present invention.
Figure 3:
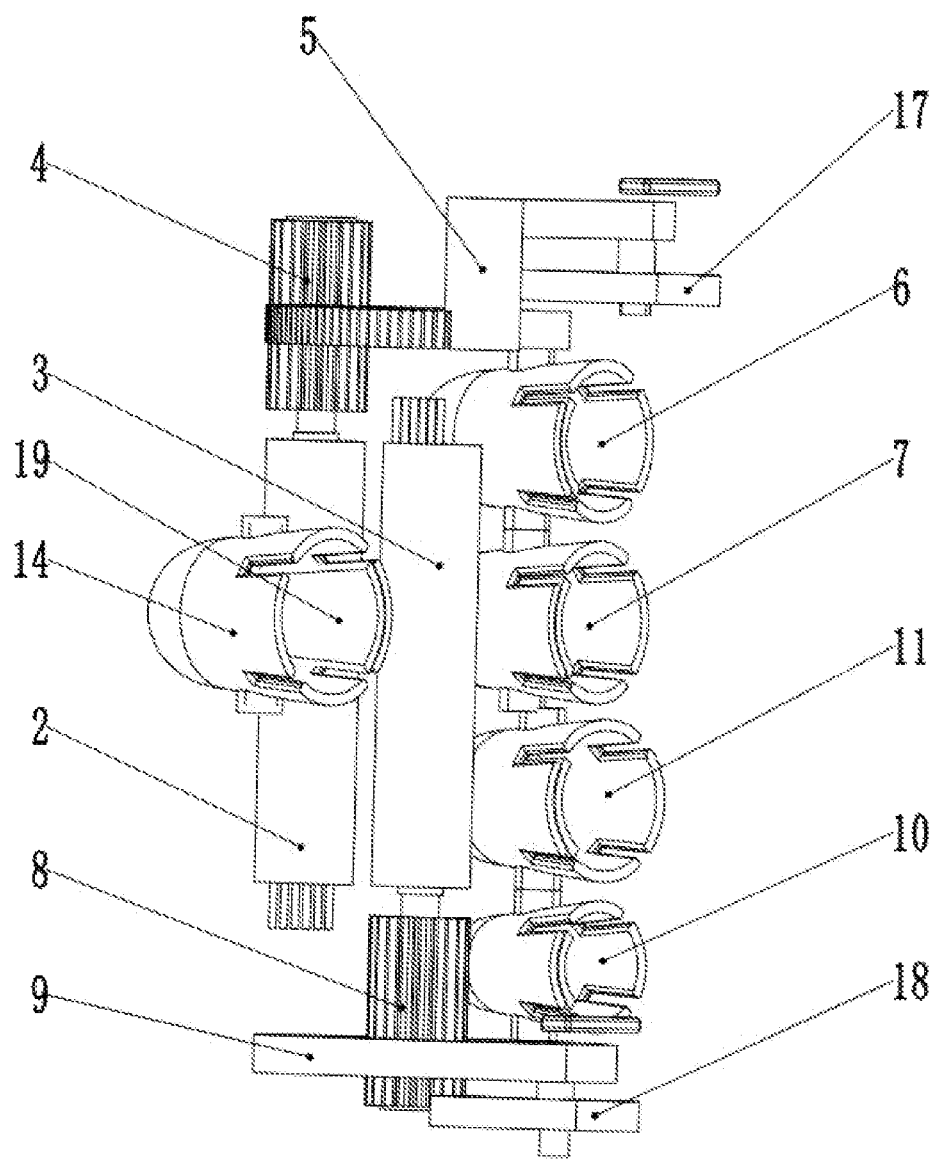
FIG. 3 is a structural diagram of the present invention after a housing is disassembled and removed.

The present invention provides an exoskeleton finger rehabilitation training apparatus. FIG. 1 to FIG. 3 show clear descriptions of the present invention. Descriptions of left-right positional relationships between components in this specification are based on the front view in FIG. 2

The present invention includes a housing 1 and a first motor 2 and a second motor 3 that are disposed inside the housing 1, a direction of an output shaft of the first motor 2 being opposite to a direction of an output shaft of the second motor 3.

The output shaft of the first motor 2 is provided with a first motor gear 4, and a right side of the first motor gear 4 is engaged with a first transmission gear 5. A rotary shaft of the first transmission gear 5 is mounted on a first support arm 12 on an outer wall of the housing 1. An edge of the first transmission gear 5 is sequentially connected to an index finger sleeve 6 and a middle finger sleeve 7 that are axially arranged.

To reduce the weight of the entire apparatus, the first transmission gear 5 is an arc-shaped external gear, and the first transmission gear 5 is connected to the rotary shaft of the first transmission gear 5 by using a first radius-connecting rod 15. In addition, the first radius-connecting rod 15 and the index finger sleeve 6 are separately located at two arc ends of the first transmission gear 5. A radian of the first transmission gear 5 is designed based on extension and clenching of fingers, so that an arc angle of the entire first transmission gear 5 can be effectively used. As such, the entire apparatus is lighter and more practical while an effect of the present invention is achieved.

The housing 1 is provided with a first passage through which the first transmission gear 5 passes. The first transmission gear 5 is provided with a first rotation limiting protrusion between the first passage and the index finger sleeve 6. When the first transmission gear 5 is rotated to an extreme position at one end, the first rotation limiting protrusion is stuck at the first passage, implementing a limiting function. When the first transmission gear 5 is rotated to an extreme position at an other end, the first radius-connecting rod 15 fixed to the first transmission gear 5 can also be stuck at the first passage, implementing a limiting function.

The output shaft of the second motor 3 is provided with a second motor gear 8, and a right side of the second motor gear 8 is engaged with a second transmission gear 9. A rotary shaft of the second transmission gear 9 is mounted on a second support arm 13 on the outer wall of the housing 1. An edge of the second transmission gear 9 is sequentially connected to a pinky sleeve 10 and a ring finger sleeve 11 that are axially arranged.

To reduce the weight of the entire apparatus, the second transmission gear 9 is an arc-shaped internal gear, and the second transmission gear 9 is connected to the rotary shaft of the second transmission gear 9 by using a second radius-connecting rod 16. In addition, the second radius-connecting rod 16 and the pinky sleeve 10 are separately located at two arc ends of the second transmission gear 9. A radian of the second transmission gear 9 is designed based on extension and clenching of fingers, so that an arc angle of the entire first transmission gear 5 can be effectively used. As such, the entire apparatus is lighter and more practical while an effect of the present invention is achieved.

The housing 1 is provided with a second passage through which the second transmission gear 9 passes. The second transmission gear 9 is provided with a second rotation limiting protrusion between the second passage and the pinky sleeve 10. When the second transmission gear 9 is rotated to an extreme position at one end, the second rotation limiting protrusion is stuck at the second passage, implementing a limiting function. When the second transmission gear 9 is rotated to an extreme position at an other end, the second radius-connecting rod 16 fixed to the second transmission gear 9 can also be stuck at the second passage, implementing a limiting function.

The housing 1 is further provided with a thumb sleeve 14, and relative positions of the thumb sleeve 14, the index finger sleeve 6, the middle finger sleeve 7, the ring finger sleeve 11, and the pinky sleeve 10 conform to an arrangement of human fingers.

In the present invention, palm sizes of different users are considered. Sizes of an upper gear and a lower gear that determine a rotation radius of the apparatus are calculated based on different joints of fingers. Table 1 shows statistical values of fingers per capita in the world as a reference, as shown below:

| Length | Thumb | Index finger | Middle finger | Ring finger | Pinky |
|---|---|---|---|---|---|
| Proximal phalanx | 42.4 | 42.7 | 43.4 | 41.4 | 32.7 |
| Middle phalanx | 31.2 | 24.2 | 28.6 | 25.6 | 18.1 |
| Distal phalanx | 27.2 | 21.4 | 23.6 | 21.2 | 19.7 |

A radius $R_1$ of the first transmission gear 5 can be calculated based on a proximal phalanx length $L_1$ and a middle phalanx length $L_2$ of the index finger:

$$L_1 \pm L_2 = R_1$$

A quantity $Z_2$ of gears of the first transmission gear 5 is calculated based on the radius $R_1$ of the first transmission gear 5, a given modulus m=1 of the upper gear, and a quantity $Z_1$ of gears of the first motor gear 4.

$$\frac{m(Z_1 + Z_2)}{2} = R_1$$

A radius $R_2$ of the second transmission gear 9 can be calculated based on a proximal phalanx length $L_3$ and a middle phalanx length $L_4$ of the pinky:

$$L_3 + L_4 = R_2$$

A quantity $Z_3$ of gears of the second transmission gear 9 is calculated based on the radius $R_2$ of the second transmission gear 9, a given modulus m=1 of the lower gear, and a quantity $Z_1$ of gears of the second motor gear 8.

$$\frac{m(Z_1 + Z_3)}{2} = R_2$$

To fit a size of a hand, the first motor 2 and the second motor 3 in the present invention need to be sequentially arranged side by side from left to right, so that a distance between the first motor gear 4 and the second motor gear 8 approximates a width of a palm. However, such an arrangement results in a distance between the first motor gear 4 and the index finger sleeve 6 greater than a distance between the second motor gear 8 and the pinky sleeve 10. Therefore, in the present invention, the first transmission gear 5 is an arc-shaped external gear, and the second transmission gear 9 is an arc-shaped internal gear, so that the radius of the first transmission gear 5 and the radius of the second transmission gear 9 more approximate the size of the hand. Moreover, the apparatus is more compact and smaller because space is effectively used.

The present invention further includes a control system. The control system includes: a single-chip microcomputer, an encoder configured to measure a rotating speed of the first motor 2 and a rotating speed of the second motor 3, a first angle sensor 17 fixed to the first support arm 12 and sleeved on the rotary shaft of the first transmission gear 5, a second angle sensor 18 fixed to the second support arm 13 and sleeved on the rotary shaft of the second transmission gear 9, and five pressure sensors 19 respectively disposed inside the thumb sleeve 14, the index finger sleeve 6, the middle finger sleeve 7, the ring finger sleeve 11, and the pinky sleeve 10; and the encoder, the first angle sensor 17, the second angle sensor 18, and the pressure sensors 19 each transmit a measurement signal to the single-chip microcomputer, and the single-chip microcomputer outputs, to the first motor 2 and the second motor 3, control signals used to control the rotating speeds of the motors.

A model of the single-chip microcomputer in this embodiment is STM32F103, a model of the first angle sensor 17 and the second angle sensor 18 is SV01A103AEA01R00.

The single-chip microcomputer receives pressure signals from the pressure sensor 19 and receives a motor rotating speed signal from the encoder, processes the signals by using a PID algorithm, and then outputs a control signal to control output forces of the motors to keep stable. In the PID algorithm, a force stability control algorithm is specifically used, and a force deviation is used to calculate a proportional integral and a differential and control a motor.

A force deviation $E_1$ of the first transmission gear 5 can be calculated based on a thumb pressure value $F_1$, an index finger pressure value $F_2$, a middle finger pressure value $F_3$, and a given force value S of the upper gear:

$$F_2 + F_3 - F_1 - S = E_1$$

Similarly, a force deviation $E_2$ of the second transmission gear 9 can be calculated based on the thumb pressure value $F_1$, a ring finger pressure value $F_4$, a pinky pressure value $F_5$, and a given force value S of the upper gear:

$$F_4 + F_5 - F_1 - S = E_2$$

By calculating the foregoing parameters, the single-chip microcomputer outputs a force stability control signal to the motors, so that the motors output more stable forces to the fingers, reducing second injury caused by the apparatus to the fingers.

The angle sensors can be configured to determine positions of the fingers, ensuring safety during operation of the apparatus. When values of the angle sensors are less than a minimum angle value, the single-chip microcomputer controls the motors to rotate clockwise. When values of the angle sensors are greater than a maximum angle value, the single-chip microcomputer controls the motors to rotate counterclockwise.

What is claimed is:

1. An exoskeleton finger rehabilitation training apparatus, comprising: a housing, a first motor and a second motor, wherein the first motor and the second motor are disposed inside the housing, and a direction of an output shaft of the first motor is opposite to a direction of an output shaft of the second motor, wherein the output shaft of the first motor is provided with a first motor gear, a right side of the first motor gear is engaged with an arc-shaped first transmission gear, and an edge of the first transmission gear is sequentially connected to an index finger sleeve and a middle finger sleeve, wherein the index finger sleeve and the middle finger sleeve are axially arranged; the output shaft of the second motor is provided with a second motor gear, a right side of the second motor gear is engaged with an arc-shaped second transmission gear, and an edge of the second transmission gear is sequentially connected to a pinky sleeve and a ring finger sleeve, wherein the pinky sleeve and the ring finger sleeve are axially arranged; an outer wall of the housing is fixed to a first support arm configured to mount a rotary shaft of the first transmission gear and a second support arm configured to mount a rotary shaft of the second transmission gear; the housing is further provided with a thumb sleeve, and relative positions of the thumb sleeve, the index finger sleeve, the middle finger sleeve, the ring finger sleeve, and the pinky sleeve adapted to conform to an arrangement of human fingers; wherein the first transmission gear is connected to the rotary shaft of the first transmission gear by using a first radius-connecting rod, and the second transmission gear is connected to the rotary shaft of the second transmission gear by using a second radius-connecting rod.

2. The exoskeleton finger rehabilitation training apparatus according to claim 1, wherein the first motor and the second motor are sequentially arranged side by side from left to right.

3. The exoskeleton finger rehabilitation training apparatus according to claim 2, wherein the first radius-connecting rod and the index finger sleeve are separately located at two arc ends of the first transmission gear, and the second radius-connecting rod and the pinky sleeve are separately located at two arc ends of the second transmission gear.

4. The exoskeleton finger rehabilitation training apparatus according to claim 3, wherein the first transmission gear is provided with a first rotation limiting protrusion between a first passage and the index finger sleeve, and the second transmission gear is provided with a second rotation limiting protrusion between a second passage and the pinky sleeve.

5. The exoskeleton finger rehabilitation training apparatus according to claim 4, further comprising a control system, wherein the control system comprises a single-chip microcomputer, an encoder configured to measure a rotating speed of the first motor and a rotating speed of the second motor, a first angle sensor fixed to the first support arm and sleeved on the rotary shaft of the first transmission gear, a second angle sensor fixed to the second support arm and sleeved on the rotary shaft of the second transmission gear, and five pressure sensors respectively disposed inside the thumb sleeve, the index finger sleeve, the middle finger sleeve, the ring finger sleeve, and the pinky sleeve; and the encoder, the first angle sensor, the second angle sensor, and the pressure sensors each transmit a measurement signal to the single-chip microcomputer, and the single-chip microcomputer outputs, to the first motor and the second motor, control signals used to control the rotating speed of the first motor and the rotating speed of the second motor.

6. The exoskeleton finger rehabilitation training apparatus according to claim 3, further comprising a control system, wherein the control system comprises a single-chip microcomputer, an encoder configured to measure a rotating speed of the first motor and a rotating speed of the second motor, a first angle sensor fixed to the first support arm and sleeved on the rotary shaft of the first transmission gear, a second angle sensor fixed to the second support arm and sleeved on the rotary shaft of the second transmission gear, and five pressure sensors respectively disposed inside the thumb sleeve, the index finger sleeve, the middle finger sleeve, the ring finger sleeve, and the pinky sleeve; and the encoder, the first angle sensor, the second angle sensor, and the pressure sensors each transmit a measurement signal to the single-chip microcomputer, and the single-chip microcomputer outputs, to the first motor and the second motor, control signals used to control the rotating speed of the first motor and the rotating speed of the second motor.

7. The exoskeleton finger rehabilitation training apparatus according to claim 2, wherein the housing is provided with a first passage and a second passage, wherein the first transmission gear passes through the first passage, and the second transmission gear passes the second passage.

8. The exoskeleton finger rehabilitation training apparatus according to claim 7, further comprising a control system, wherein the control system comprises a single-chip microcomputer, an encoder configured to measure a rotating speed of the first motor and a rotating speed of the second motor, a first angle sensor fixed to the first support arm and sleeved on the rotary shaft of the first transmission gear, a second angle sensor fixed to the second support arm and sleeved on the rotary shaft of the second transmission gear, and five pressure sensors respectively disposed inside the thumb sleeve, the index finger sleeve, the middle finger sleeve, the ring finger sleeve, and the pinky sleeve; and the encoder, the first angle sensor, the second angle sensor, and the pressure sensors each transmit a measurement signal to the single-chip microcomputer, and the single-chip microcomputer outputs, to the first motor and the second motor, control signals used to control the rotating speed of the first motor and the rotating speed of the second motor.

9. The exoskeleton finger rehabilitation training apparatus according to claim 2, further comprising a control system, wherein the control system comprises a single-chip microcomputer, an encoder configured to measure a rotating speed of the first motor and a rotating speed of the second motor, a first angle sensor fixed to the first support arm and sleeved on the rotary shaft of the first transmission gear, a second angle sensor fixed to the second support arm and sleeved on the rotary shaft of the second transmission gear, and five pressure sensors respectively disposed inside the thumb sleeve, the index finger sleeve, the middle finger sleeve, the ring finger sleeve, and the pinky sleeve; and the encoder, the first angle sensor, the second angle sensor, and the pressure sensors each transmit a measurement signal to the single-chip microcomputer, and the single-chip microcomputer outputs, to the first motor and the second motor, control signals used to control the rotating speed of the first motor and the rotating speed of the second motor.

10. The exoskeleton finger rehabilitation training apparatus according to claim 1, further comprising a control system, wherein the control system comprises a single-chip microcomputer, an encoder configured to measure a rotating speed of the first motor and a rotating speed of the second motor, a first angle sensor fixed to the first support arm and sleeved on the rotary shaft of the first transmission gear, a second angle sensor fixed to the second support arm and sleeved on the rotary shaft of the second transmission gear, and five pressure sensors respectively disposed inside the thumb sleeve, the index finger sleeve, the middle finger sleeve, the ring finger sleeve, and the pinky sleeve; and the encoder, the first angle sensor, the second angle sensor, and the pressure sensors each transmit a measurement signal to the single-chip microcomputer, and the single-chip microcomputer outputs, to the first motor and the second motor, control signals used to control the rotating speed of the first motor and the rotating speed of the second motor.

11. The exoskeleton finger rehabilitation training apparatus according to claim 10, wherein a model of the single-chip microcomputer is STM32F103, and a model of the first angle sensor and the second angle sensor is SV01A103AEA01R00.

* * * * *